United States Patent
Flo et al.

(10) Patent No.: US 9,517,032 B2
(45) Date of Patent: *Dec. 13, 2016

(54) SENSOR OVER-MOLD SHAPE

(75) Inventors: Daniel S. Flo, St. Louis Park, MN (US); James K. Carney, Falcon Heights, MN (US); Kamal Deep Mothilal, Minneapolis, MN (US); Jon D. Schell, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 1103 days.

This patent is subject to a terminal disclaimer.

(21) Appl. No.: 13/362,371

(22) Filed: Jan. 31, 2012

(65) Prior Publication Data

US 2013/0197336 A1    Aug. 1, 2013

(51) Int. Cl.
*G01L 7/00* (2006.01)
*A61B 5/00* (2006.01)
*A61B 5/0215* (2006.01)
*G01L 19/14* (2006.01)

(52) U.S. Cl.
CPC ........... *A61B 5/6861* (2013.01); *A61B 5/0215* (2013.01); *A61B 5/6876* (2013.01); *A61B 2560/0406* (2013.01); *A61B 2562/0247* (2013.01); *A61B 2562/162* (2013.01); *A61B 2562/18* (2013.01); *G01L 19/146* (2013.01)

(58) Field of Classification Search
None
See application file for complete search history.

(56) References Cited

U.S. PATENT DOCUMENTS

| 3,418,853 A | 12/1968 | Curtis |
| 3,748,623 A | 7/1973 | Millar |
| 4,507,973 A | 4/1985 | Barr |
| 4,901,735 A | 2/1990 | von Berg |
| 5,067,491 A | 11/1991 | Taylor, II et al. |
| 5,353,800 A | 10/1994 | Pohndorf et al. |
| 5,535,752 A * | 7/1996 | Halperin et al. .............. 600/483 |
| 5,540,731 A | 7/1996 | Testerman |

(Continued)

FOREIGN PATENT DOCUMENTS

| CN | 1292084 A | 4/2001 |
| CN | 101983031 A | 3/2011 |
| CN | 102137620 A | 7/2011 |

OTHER PUBLICATIONS

Office Action mailed Sep. 12, 2014 for U.S. Appl. No. 13/362,270.
(Continued)

*Primary Examiner* — Andre Allen
(74) *Attorney, Agent, or Firm* — Evans M. Mburu

(57) ABSTRACT

An implantable sensor module and medical device includes a housing having an inner shell having a thickness extending between an inner wall and an outer wall and an outer layer, wherein the inner shell and the outer layer form a substantially flat portion. A shoulder extends adjacent to a diaphragm to extend the outer layer laterally away from a central medial line extending between edges of the diaphragm. A recess portion is formed between the diaphragm and an inner side of the outer layer, and an over-fill channel is formed by the outer layer extending through the outer layer from an opening formed at the outer wall to an opening formed along the inner side of the outer layer extending along the substantially flat portion.

24 Claims, 6 Drawing Sheets

(56) References Cited

U.S. PATENT DOCUMENTS

| | | |
|---|---|---|
| 5,554,176 A | 9/1996 | Maddison et al. |
| 5,564,434 A * | 10/1996 | Halperin et al. ............... 600/488 |
| 5,755,766 A | 5/1998 | Chastain et al. |
| 6,221,024 B1 | 4/2001 | Miesel |
| 6,331,161 B1 | 12/2001 | Chesney et al. |
| 6,572,543 B1 | 6/2003 | Christopherson et al. |
| 6,580,946 B2 | 6/2003 | Struble |
| 7,231,259 B2 | 6/2007 | Jenney et al. |
| 7,231,829 B2 | 6/2007 | Schugt |
| 7,367,951 B2 | 5/2008 | Bennett |
| 7,591,185 B1 | 9/2009 | Mothilal |
| 7,614,308 B2 | 11/2009 | Berner et al. |
| 8,127,618 B1 * | 3/2012 | Zhao et al. ..................... 73/754 |
| 8,613,702 B2 | 12/2013 | Feer |
| 8,723,361 B2 | 5/2014 | Flegel |
| 9,005,134 B2 | 4/2015 | Flo et al. |
| 9,131,858 B2 | 9/2015 | Flo et al. |
| 2006/0116588 A1 | 6/2006 | Archibald |
| 2009/0248125 A1 * | 10/2009 | Brostrom ..................... 607/119 |
| 2009/0299429 A1 | 12/2009 | Mayotte |
| 2010/0076519 A1 | 3/2010 | Kornet |
| 2011/0257593 A1 * | 10/2011 | Kalpin et al. ................. 604/111 |
| 2012/0197155 A1 * | 8/2012 | Mattes et al. ................. 600/561 |
| 2013/0197336 A1 * | 8/2013 | Flo et al. ..................... 600/373 |
| 2013/0197396 A1 * | 8/2013 | Flo et al. ..................... 600/587 |

OTHER PUBLICATIONS

PCT/US2012/066171 PCT Notification of Transmittal of the International Search Report and the Written Opinion of the International Searching Authority, mailed Mar. 12, 2013, 11 pages.

Chinese office action for application No. 201280068575.6, English translation, mailed Oct. 10, 2015, 5 pages.

Chinese office action for application No. 201280068575.6, mailed Oct. 10, 2015, 6 pages.

Communication from EPO for application No. 12805490.5, mailed Sep. 3, 2015, 4 pages.

* cited by examiner

SENSOR OVER-MOLD SHAPE

CROSS-REFERENCE TO RELATED APPLICATION

Cross-reference is hereby made to the commonly-assigned related U.S. application Ser. No. 13/362,270, entitled "SENSOR OVER-MOLD SHAPE," to Flo et al., and U.S. application Ser. No. 13/362,305, entitled "SENSOR OVER-MOLD SHAPE," to Flo et al., both filed concurrently herewith and incorporated herein by reference in its entirety.

FIELD OF THE DISCLOSURE

The disclosure relates generally to medical devices and, in particular, to a housing of an implantable medical sensor module that includes a diaphragm.

BACKGROUND

Implantable medical sensors are used for sensing physiological signals in a patient for use in diagnosing a disease state or managing patient therapies. Among examples of implantable sensors are pressure sensors, flow sensors, acoustical sensors, and optical sensors. A pressure sensor positioned in the heart or in a blood vessel is highly useful in monitoring cardiovascular conditions, such as heart failure, hypertension, arrhythmias or other conditions. For example, a capacitive pressure sensor includes one capacitor electrode along a diaphragm and a second capacitor electrode substantially parallel to and held a few micrometers from the electrode of the diaphragm. An "air gap" provides insulation between the two parallel electrodes. As the blood pressure changes, the diaphragm flexes closer to or further away from the second electrode, resulting in a change in capacitance. The capacitance can be measured in many ways and can be converted to pressure using a calibration algorithm.

Some sensors can produce a baseline signal that drifts over time or presents a baseline offset. The causes of drift or offset can vary and lead to erroneous measurements determined from the sensor signal, particularly for calibrated sensors such as a calibrated pressure sensor. Accordingly, sensor designs are needed that reduce the potential for error in chronically implanted sensors.

DETAILED DESCRIPTION

In the following description, references are made to illustrative embodiments. It is understood that other embodiments may be utilized without departing from the scope of the disclosure.

Figure 1A:
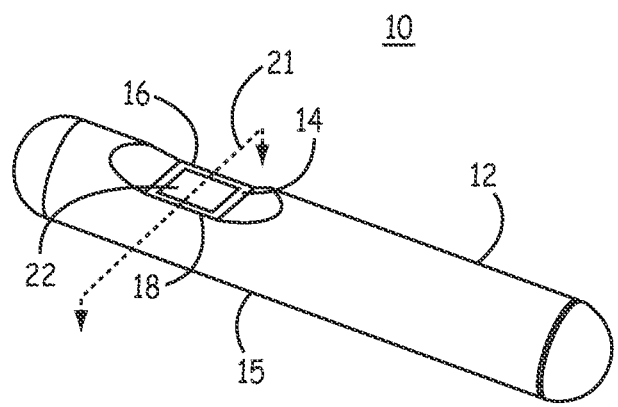
FIG. 1A is a perspective view of a sensor module including a housing enclosing a sensor transducer and associated circuitry.

FIG. 1A is a perspective view of a pressure sensor module 10 including a housing 12 enclosing a sensor transducer and associated circuitry (not shown in FIG. 1A). The housing 12 includes a substantially flat portion 14 extending between a first outer side 16 and a second outer side 18. A flexible diaphragm 22 extends along substantially flat portion 14 between outer sides 16 and 18. Diaphragm 22 is exposed to external pressures applied to the outer surface of flat portion 14. In the embodiment shown, the housing 12 is substantially cylindrical and thus includes a rounded or curved wall 15 opposing the substantially flat portion 14. In other embodiments, the housing may be configured as other rounded, prismatic, or geometric shapes and may or may not be elongated, but generally includes a substantially flat portion along which the sensor diaphragm extends and a curved or substantially flat side opposing the flat portion.

Sensor module 10 is shown as a wireless sensor which may be implanted within the blood stream or blood volume or at any extravascular location targeted for monitoring a physiological signal. Sensor module 10 may include fixation elements or members attached to housing 12 to facilitate fixation of module 10 at a desired implant site. Fixation members are not explicitly shown in FIG. 1, but it is recognized that various embodiments may include any type of fixation members used to anchor implantable medical devices at an anatomical location.

Figure 1B:
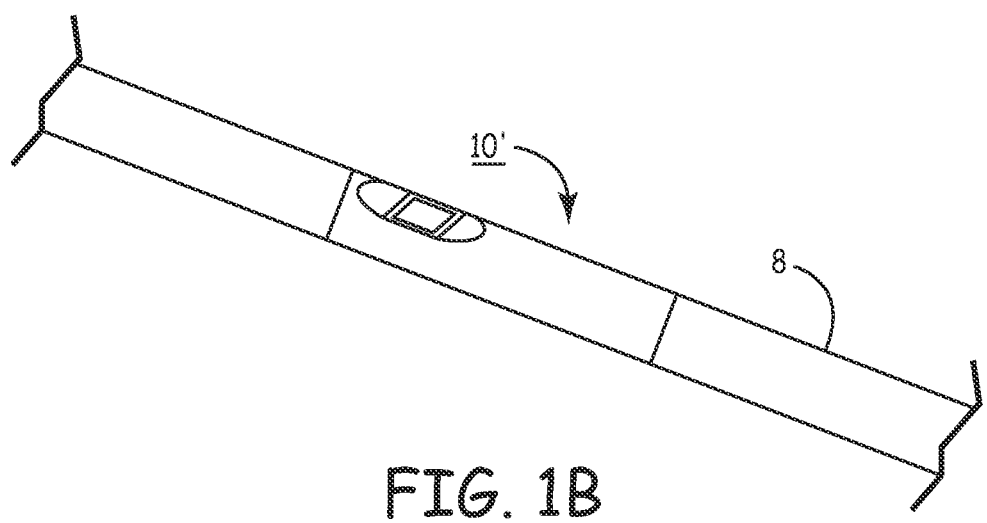
FIG. 1B is a partial perspective view of a sensor module carried by an elongated flexible medical lead body.

In other embodiments, as shown in FIG. 1B, a sensor module 10' may be carried by an elongated flexible medical lead body 8. Sensor module 10' may correspond generally to sensor module 10 shown in FIG. 1A with the exception of being coupled to the lead body 8 and may be configured for wireless or wired signal transmission to an associated medical device. Elongated lead body 8 may additionally carry other sensors or electrodes and typically includes elongated electrical conductors extending between sensors and/or electrodes carried by the lead body 8 and a proximal electrical connector assembly (not shown). The connector assembly is adapted for connection to a medical device such as a pacemaker, cardioverter/defibrillator, neurostimulator, monitoring device or the like to provide electrical connection between sensors and/or electrodes carried by the lead body 8 and the associated medical device.

Examples of implantable devices that sensor module 10 may be used with, in either a wireless configuration as shown in FIG. 1A or a lead-based configuration as shown in FIG. 1B, are generally disclosed in commonly-assigned U.S. Publication No. 2010/0076819 (Kornet), U.S. Pat. No. 5,540,731 (Testerman), U.S. Pat. No. 7,367,951 (Bennett), U.S. Pat. No. 6,580,946 (Struble), and U.S. Publication No. 2009/0299429 (Mayotte), all of which references are incorporated herein by reference in their entirety. A capacitive pressure sensor is generally disclosed in commonly-assigned U.S. Pat. No. 5,535,752 (Halperin), hereby incorporated herein by reference in its entirety.

Figure 2A:
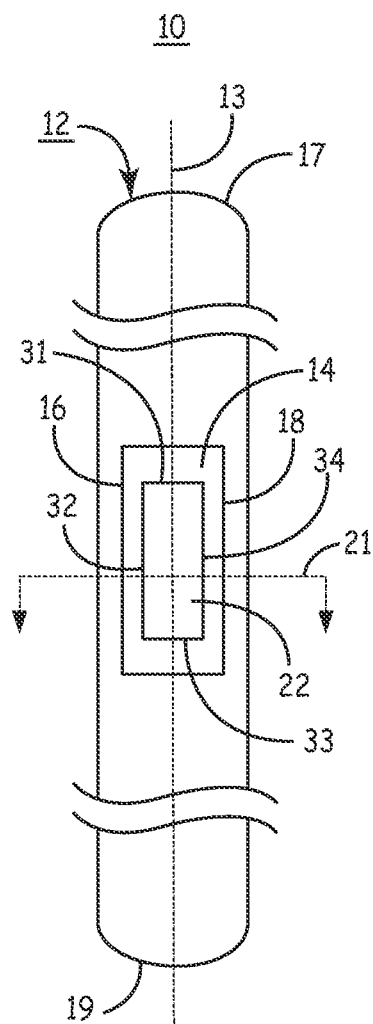
FIG. 2A is a top plan view of the sensor module of FIG. 1A.

FIG. 2A is a top plan view of the sensing module 10 of FIG. 1A. Housing 12 includes an outer wall 9 having a cut-out portion 11 formed in the outer wall 9. The cut-out portion 11 is formed having a first longitudinal outer side 16 and a second longitudinal outer side 18, both extending longitudinally along the sensing module 10, and a first lateral outer side 23 and a second lateral outer side 25 extending laterally along the sensing module 10 between the first outer side 16 and the second outer side 18. A substantially flat portion 14 is formed within the cut-out portion 11 along which diaphragm 22 extends. Diaphragm 22 has opposing longitudinal edges 32 and 34 separated by a width of the diaphragm 22 and defined by opposing lateral edges 31 and 33. Opposing longitudinal edges 32 and 34 extend adjacent to, and in relative close proximity of, outer sides 16 and 18 of cut-out portion 11 of housing 12. Longitudinal edges 32 and 34 extend substantially parallel with the longitudinal axis 13 of the elongated sensor module 10. In the embodiment shown, longitudinal axis 13 also defines a medial plane between diaphragm edges 32 and 34, although diaphragm 22 is not necessarily centered on a central longitudinal axis of the sensor module in all embodiments. Outer sides 16 and 18 extend substantially parallel to diaphragm edges 32 and 34, respectively. Outer sides 16 and 18 extend between housing ends 17 and 19.

Figure 2B:
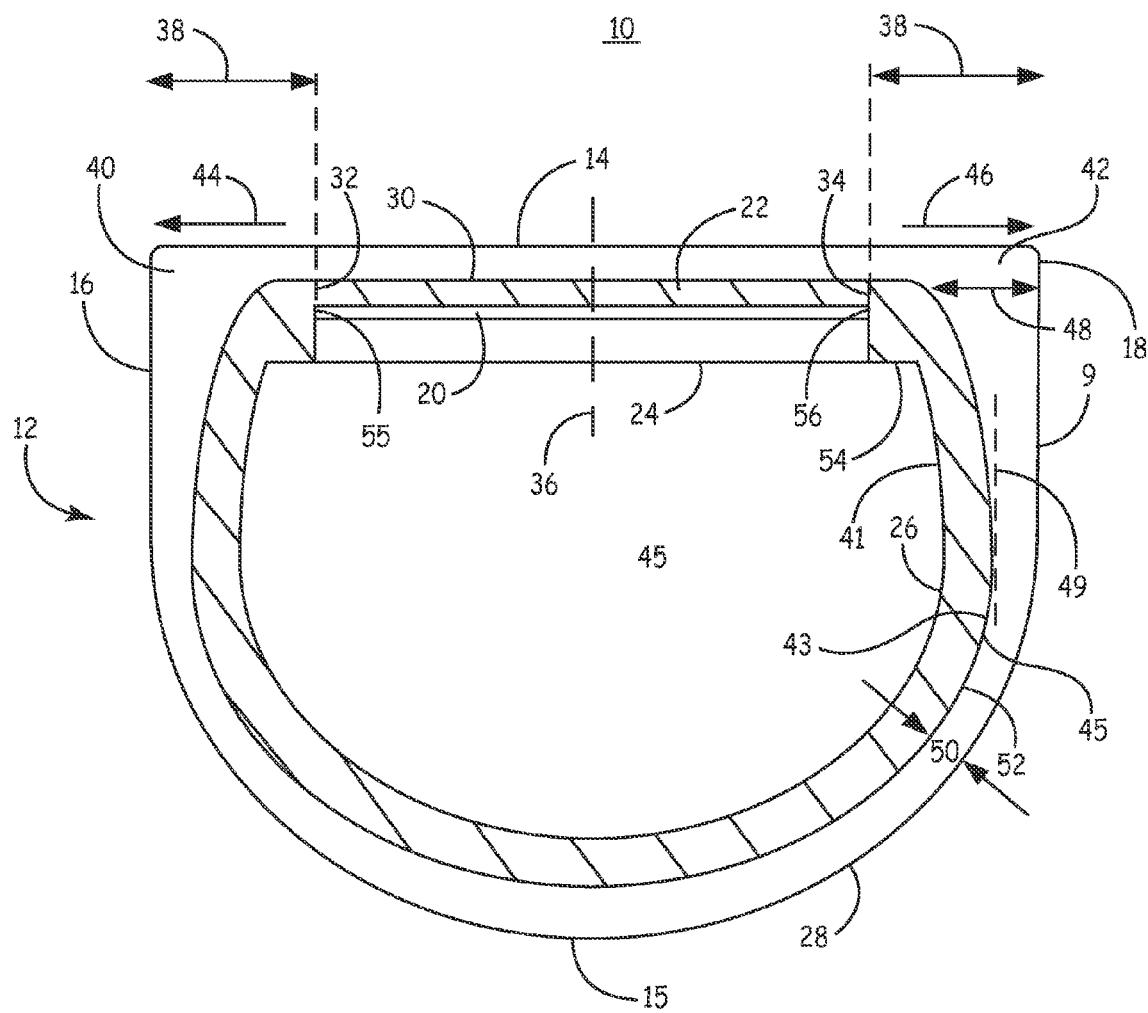
FIG. 2B is a sectional view of the sensor module of FIG. 1A taken along a lateral plane through a diaphragm of the sensor module.

FIG. 2B is a sectional view of substantially flat portion 14 of sensor module 10, taken along a lateral plane 21 as shown in FIG. 2A. In some embodiments housing 12 includes an inner shell 26, which may be substantially rigid, and an outer layer 28 that conforms to and extends around and encloses inner shell 26. Shell 26 may be a metallic casing, such as an electrically conductive titanium shell. Shell 26 includes a substantially flat side 54 opposing a curved or partial cylindrical side 52 in one embodiment. In some embodiments, shell 26 is a machined component having a thin diaphragm 22 formed along substantially flat side 54. Shell 26 has a thickness extending between an inner wall 41 of shell 26 and an outer wall 43 of shell 26. A machining process is used to form diaphragm 22 by removing material from the inner side of substantially flat side 54, thereby defining inner sidewalls 55 and 56. The machining process is performed according to specifications defining the width and thickness of diaphragm 22. Diaphragm 22 extends between inner sidewalls 55 and 56 such that the distance between inner sidewalls 55 and 56 defines the width of diaphragm 22, and diaphragm edges 32 and 34 are aligned with inner sidewalls 55 and 56. The inner surface of substantially flat side 54 may be machined to form diaphragm 22 having a thickness of approximately 0.001 inches in one example. In various embodiments, shell 26 may be formed from one or more components coupled together and may include one or more materials to form the substantially flat side 54, diaphragm 22 and opposing side 52.

Outer layer 28 may be a flexible layer of molded silicone, polyurethane or other biomedical polymeric material having an internal contour that corresponds to the exterior contour of shell 26 and has elastic properties that allow it to be stretched over shell 26 and snugly surround and conform to shell 26. Outer layer 28 has a thickness extending between an inner side 45 of outer layer 28, which is engaged against the outer wall 43 of the inner shell 26, and the outer wall 9 of the housing 12. In various embodiments, outer layer 28 may be applied by dip coating, formed through injection molding, or other appropriate manufacturing methods. A medical adhesive coating, e.g. silicone medical adhesive, may be applied along the interface 30 between flexible layer 28 and diaphragm 22 as well as the interface between other areas of shell 26 and outer layer 28 to securely couple outer layer 28 to shell 26.

Outer layer 28 covers diaphragm 22 but is provided with a thickness and flexibility that allows force applied to the external surface of outer layer 28 over the area of the diaphragm 22 to be transferred to the diaphragm 22. This allows a pressure sensitive transducer included in hybrid circuit 24 to generate a signal correlated to changes in pressure applied to diaphragm 22.

Hybrid circuit 24 including a signal transducer and associated circuitry is positioned beneath diaphragm 22 and enclosed by housing 12. Diaphragm 22, formed from electrically conductive material, is one electrode of an air-gap capacitor in one embodiment. The circuit 24 includes a second electrode of the air-gap capacitor on the upper surface of the circuit 24, facing the diaphragm 22 but separated by an insulative layer 20, which may be an air gap or filled with another insulating material. Although the term "air gap" is used herein to describe the capacitor formed by diaphragm 22 and a second electrode on circuit 24, the insulative layer 20 between diaphragm 22 and the second capacitor electrode along circuit 24 may be filled with air, vacuum, a mixture of gases, or a flexible polymer. The capacitor formed by the two electrodes separated by insulative layer 20 produces a varying capacitance in response to movement of diaphragm 22 caused by changes in external pressure applied to diaphragm 22.

In other embodiments, hybrid circuit 24 includes any signal transducer responsive to movement, force or pressure applied to diaphragm 22 which may include fluid pressure, sound waves, or other mechanical forces. For example, a piezoresistive sensor, acoustical sensor, optical sensor or any other sensor that includes a diaphragm, which may or may not require an insulative layer beneath the diaphragm, may benefit from the housing shapes and designs disclosed herein.

The body's foreign body response will naturally result in tissue encapsulation of sensor 10 when it is implanted chronically. The tissue encapsulation or "scar" is generally fibrous tissue and can alter the response of the implantable sensor 10 over time. As the scar tissue ages it can shrink or contract. The inventors of the present application have discovered that shrinking of the tissue encapsulation around the external surface of housing 12 (particularly along outer layer 28 over the area of diaphragm 22) generates a contact pressure over the diaphragm 22. The contact pressure can increase as the tissue encapsulation ages and can cause baseline pressure offset or drift of chronically recorded sensor signals. This phenomenon of tissue encapsulation and contraction of the scar tissue can be a potential source of error in any chronically implantable medical sensor that utilizes a flexible or moving diaphragm responsive to pressure or mechanical forces. Chronic monitoring of a physiological signal, blood pressure for example, may become erroneous due to contact pressure generated by the tissue encapsulation of the sensor 10.

To reduce contact pressures over diaphragm 22 caused by encapsulating tissue, housing 12 includes shoulders 40 and 42 which extend outer sides 16 and 18 laterally away from a medial line 36 of diaphragm 22, extending medially between diaphragm edges 32 and 34. As used herein, the term "laterally" when used with respect to a medial line or medial plane of a sensor diaphragm refers to a direction away from the medial line or plane of the diaphragm. For example, "laterally" with regard to medial line 36 of diaphragm 22 is a direction away from the medial line 36 as indicated by arrows 44 and 46 extending toward respective housing outer sides 16 and 18. In some embodiments, a shoulder that extends an outer side laterally away from the diaphragm medial line is defined by a portion of the housing having a thickened wall adjacent the diaphragm edges 32 and 34, i.e. extending laterally from diaphragm edges 32 and 34. In other words, the shoulder comprises a portion of the housing having a greater wall thickness laterally adjacent edges 32 and 34 than a housing wall thickness along other portions of the housing such as along the flat portion 14 and an opposing wall 15.

In one embodiment, lateral shoulders 40 and 42 are defined by an outer layer 28 having a variable thickness in the embodiments shown. For example, the thickness 48 of outer layer 28 existing at the level of diaphragm 22, i.e. adjacent diaphragm edges 32 and 34, is greater than the outer layer thickness 50 along other portions of housing 12, e.g. along flat portion 14 and opposing wall 15. This increased thickness of the outer layer 28 between diaphragm longitudinal edges 32 and 34 and outer sides 16 and 18 positions the outer sides 16 and 18 laterally away from medial line 36 and diaphragm longitudinal edges 32 and 34 as compared to a design having a uniform thickness of outer layer 28 conforming to the curved portion 52 of shell 26. In a specific example, the outer layer 28 has a wall thickness 48 defining shoulder 42 such that outer side 18 extends parallel to a plane 49 tangential to a widest point of a curved side 52 of shell 26. Additionally, thickness 48 may define shoulder 42 such that outer side 18 meets flat portion 14 approximately perpendicularly. The same or similar configuration may be applied to shoulder 16.

In other embodiments, shoulders 40 and 42 may be defined by a variable thickness shell 26 which may include a greater thickness between diaphragm 22 and outer sides 16 and 18 of housing 12 than along other portions of shell 26. In this case, outer layer 28 may be formed having a uniform thickness conforming to shell 26. In still other embodiments, both shell 26 and outer layer 28 may be provided with a thickness between diaphragm edges 32 and 34 and outer sides 16 and 18, respectively, that contribute to forming shoulders 40 and 42 having a greater overall wall thickness than other portions of housing 12, which move outer sides 16 and 18 laterally outward with respect to medial line 36 as compared to the relative position of outer sides 16 and 18 if both shell 26 and outer layer 28 were of uniform thickness and follow a rounded, cylindrical or other geometric profile that narrows as it intersects or reaches flat side 54 or approaches diaphragm edges 32 and 34 in relative close proximity. In the embodiments shown herein, housing 12 has a generally elongated cylindrical or rounded shape which can be smoothly advanced along a blood vessel to an implant location. It is contemplated, however that housing 12 may be formed with other geometrical cross-sectional shapes than the substantially cylindrical shape shown in FIG. 1, such as a generally rectangular cross-section.

It is further contemplated that the housing 12 can be provided having a uniform thickness in some embodiments but having a distance 38 between each of diaphragm edges 32 and 34 and respective outer sides 16 and 18 that extends outer sides 16 and 18 laterally away from medial line 36. The distance 38 between diaphragm edges 32 or 34 and respective outer sides 16 or 18 can be controlled by specifying the width of diaphragm 22, i.e. resulting lateral thickness of sidewalls 55 and 56, thickness of shell 26 and thickness of outer layer 28, and overall width of the sensor module. The distance 38 between diaphragm edges 32 and 34 and respective outer sides 16 and 18 is specified to reduce contact pressure occurring over the diaphragm 22 and at the diaphragm edges 32 and 34 due to tissue encapsulation shrinkage as will be further described below.

Figure 3:
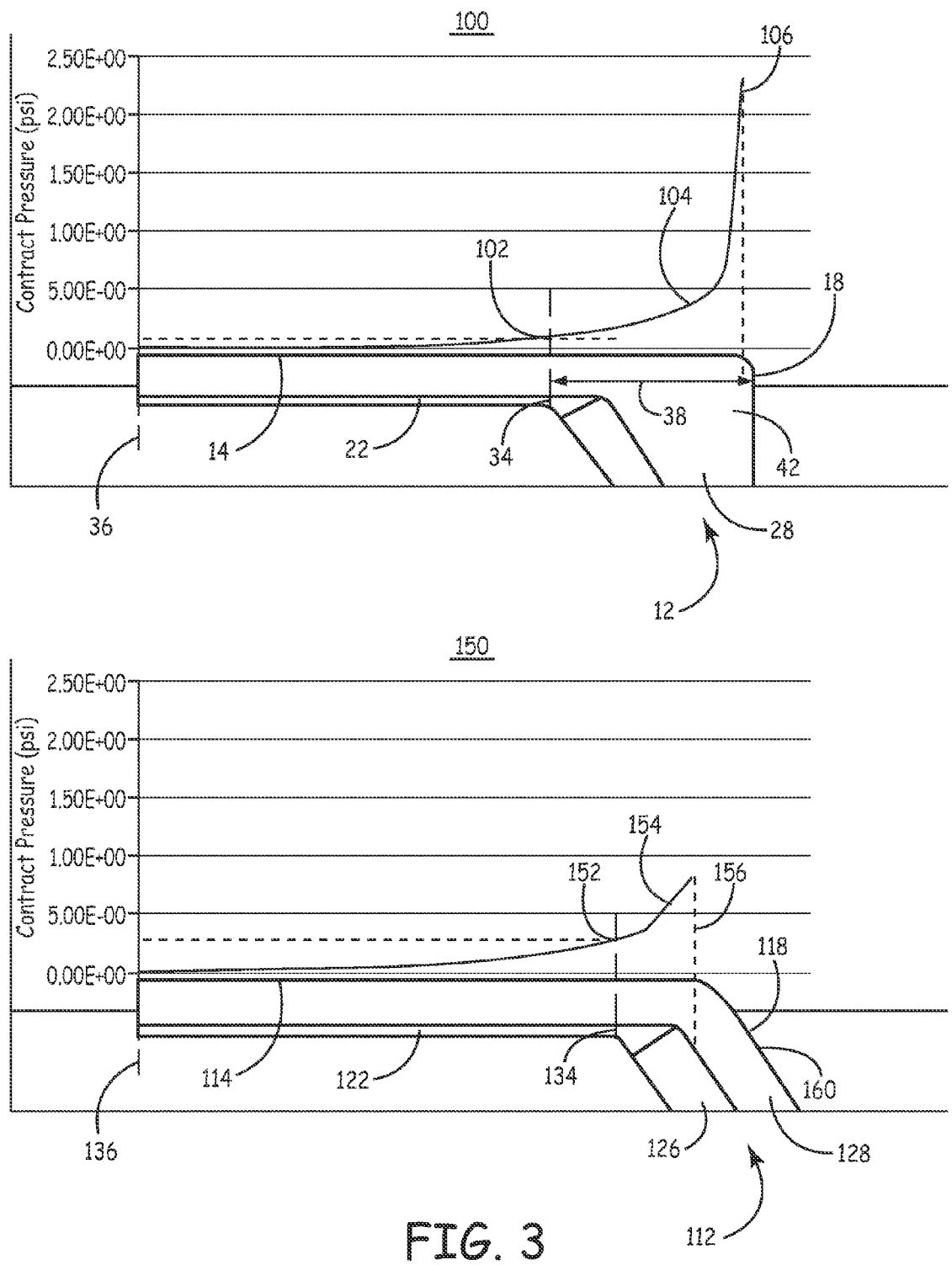
FIG. 3 depicts plots of contact pressure on a sensor diaphragm computed using a mathematical model of the effect of tissue encapsulation on two different sensor housing shapes.

FIG. 3 depicts plots 100 and 150 of contact pressure along a sensor module diaphragm computed using a mathematical model of the effect of tissue encapsulation on two different sensor housing shapes. Plot 100 depicts contact pressure expected along flat portion 14 of housing 12 shown in FIG. 2 caused by tissue encapsulation around sensor module 10. Contact pressure 104 is plotted over distance from diaphragm medial line 36 to housing outer side 18. Shoulder 42, defined by outer layer 28 having a variable wall thickness, moves a maximum contact pressure 106 laterally away from diaphragm edge 34, thereby reducing the magnitude of the contact pressure 102 occurring at edge 34.

Plot 150 depicts contact pressure 154 expected along a flat portion 114 of a housing 112 that does not include a shoulder defined by a variable thickness housing extending outer side 118 laterally away from medial plane 136 of diaphragm 122. Instead, a rounded or cylindrical wall 160 opposing flat portion 114 intersects flat portion 114 with a continuous wall thickness of both shell 126 and flexible layer 128. The rounded profile results in an outer side 118 that is relatively closer to medial line 136 than outer side 18 is from respective medial line 36 in housing 12 as shown in plot 100. The maximum contact pressure 156 occurs closer to diaphragm edge 134. The contact pressure 152 reached at diaphragm edge 134 (plot 150) is significantly greater than the contact pressure 102 at diaphragm edge 34 of housing 12 (plot 100). The slope of contact pressure 154 over the area of diaphragm 122 is observed to be greater than the slope of contact pressure 104 over diaphragm 22 resulting in greater baseline offset error associated with housing 112 due to tissue encapsulation shrinkage. In plots 100 and 150, the contact pressure curves 104 and 154 are expected to be symmetrical about medial lines 36 and 136.

Contact pressures that are produced near a medial line or center of the diaphragm will produce significantly more offset than contact pressures near the edge of a diaphragm. Therefore, goals of a housing design shaped to reduce diaphragm contact pressure caused by tissue encapsulation shrinkage can include reducing the amplitude of the contact pressure and pushing the maximum contact pressure toward or beyond the edge of the diaphragm, thereby reducing contact pressure at and near a medial line or center of the diaphragm as well as at the diaphragm edges.

In one embodiment, shoulder 42 extends housing outer side 18 laterally away from diaphragm edge 34 by a distance 38 that causes approximately 80% or more of the area under the contact pressure curve 104 to be off of the diaphragm 22. In other words the area under the contact pressure curve 104 between medial line 36 and edge 34, i.e. over diaphragm 22, is approximately 20% or less of the total area under the contact pressure curve 104. The area under contact pressure curve 104 between edge 34 and outer side 18, i.e. off of diaphragm 22, is approximately 80% or more of the total area under contact pressure curve 104. In this way, the contact pressure is substantially moved off of the diaphragm 22 and over a non-diaphragm area of the housing 12.

In another embodiment, shoulder 42 is designed to reduce the area under contact pressure curve 104 over diaphragm 22 to be approximately 10% or less of the total area under the contact pressure curve 104 such that 90% of the contact pressure due to tissue encapsulation shrinkage is applied to the housing off of the diaphragm. In comparison, when housing 112 does not have a shoulder extending outer edge 118 away from diaphragm edge 134, a substantial portion of the area under contact pressure curve 154 is over the diaphragm 122.

In still other embodiments, shoulder 42 extends housing outer side 18 laterally away from diaphragm edge 34 by a distance 38 to cause the contact pressure 102 at the diaphragm longitudinal edge 34 to be less than a predetermined percentage of the maximum contact pressure 106. For example, shoulder 42 may reduce contact pressure 102 at diaphragm edge 34 to less than approximately 20 percent, or another desired percentage, of the maximum contact pressure 106.

Figure 4:
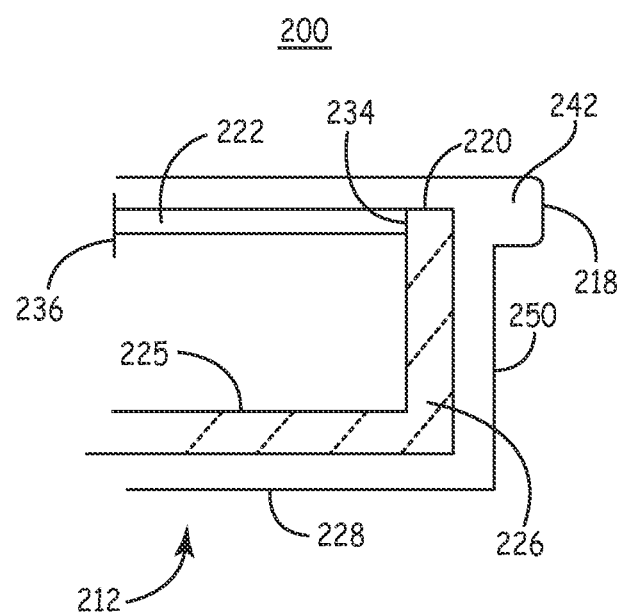
FIG. 4 is a partial sectional view of a sensor module according to an alternative embodiment.

FIG. 4 is a partial sectional view of a sensor module 200 according to an alternative embodiment. Housing 212 includes an inner shell 226 having a diaphragm 222 extending along one side 220 of inner shell 226. A substantially flat side 225 opposes diaphragm 222 and side 220 in this embodiment such that housing 212 has a substantially rectangular cross-section. Housing 212 further includes an outer flexible layer 228 that conforms to shell 222 and defines shoulder 242 as a laterally protruding flange that extends outer side 218 laterally away from medial line 236 of diaphragm 222.

In various embodiments, a shoulder 242 that extends a housing outer side 218 laterally away from medial line 236 and longitudinal edge 234 of the sensor diaphragm 222, may be formed as a flange, ring, outcropping, or other projection. Such a projection will reduce contact pressure due to tissue encapsulation shrinkage over the area of the diaphragm 222 as compared to a relatively more narrow profile of the housing 212 adjacent diaphragm edge 234 that results in outer side 218 being relatively closer to the diaphragm medial line 236 than in the embodiment shown. Outer side 218 of shoulder 242 formed by the laterally extending protrusion or flange extends laterally outward with respect to an outer surface 250 of housing 212. It is contemplated that in other embodiments shell 226 may be formed with a flange or protruding portion defining a shoulder extending laterally away from longitudinal edge 234. In such embodiments, outer layer 228 can be formed with an approximately uniform wall thickness conforming to shell 226.

Figure 5:
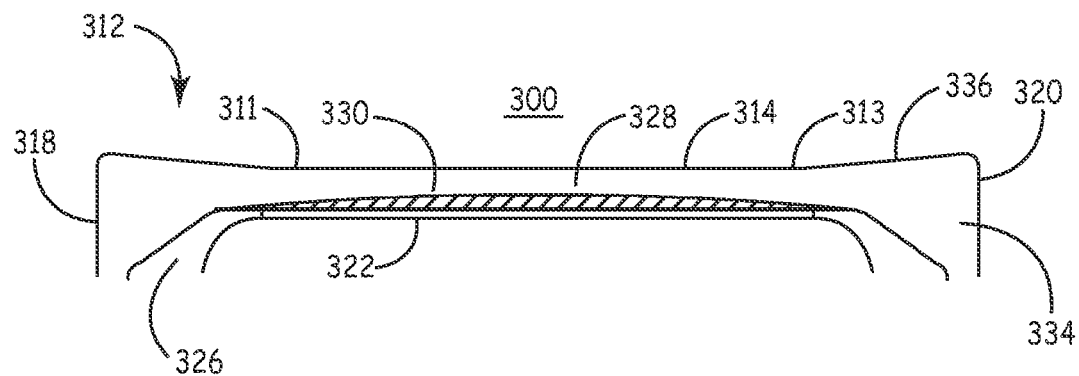
FIG. 5 is a partial sectional view of a sensor module according to another embodiment.

FIG. 5 is a partial sectional view of a sensor module 300 according to another embodiment. A sensor housing 312 includes an inner shell 326 along which diaphragm 322 extends, as generally described above. Housing 312 further includes an outer layer 328, which may be flexible, surrounding and conforming to shell 326 as generally described above. As illustrated in FIG. 5, a coating 330 of medical adhesive (shown in hashed lines) may be applied at an interface between outer layer 328 and shell 326. The medical adhesive coating 330 may cause a bulging of outer surface 314 of housing 312, which later can lead to increased contact pressure over diaphragm 322 due to tissue encapsulation shrinkage. Accordingly, in one embodiment, outer layer 328 is formed having a recessed outer surface 314, extending from a first edge 311 to a second edge 313 so as to be positioned at least along a portion of outer layer 328 that extends over diaphragm 322, where bulging is expected to occur due to application of medical adhesive coating 330. The outer layer 328 is shown to include a shoulder 334 as generally described above but in this embodiment outer layer 328 includes a sloping upper surface 336 meeting recessed outer surface 314. Recessed outer surface 314 will generally be defined by a continuous wall thickness over diaphragm 322 which is less than the wall thickness of the outer layer 328 along the portion of outer layer 328 that does not extend over diaphragm 322, i.e., recessed outer surface 314 wall thickness is less than the wall thickness along shoulder 334. In one embodiment, recessed outer surface 314 may have a length and a width of the recessed portion that is approximately the same as the length and the width of the diaphragm 322 to reduce contact pressure on diaphragm 322 due to tissue encapsulation shrinkage. In this way, the thickness of outer layer 328 decreases from an outer side 318, 320 of the device toward respective edges 311, 313 of recessed outer surface to form the sloping upper surface 336.

Figure 6:
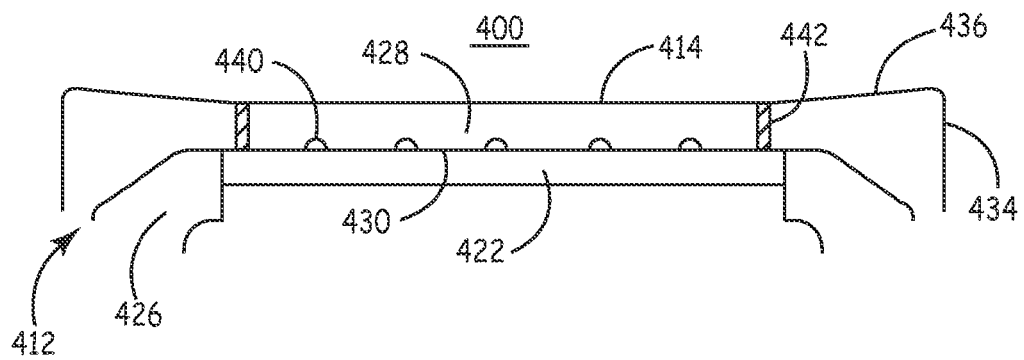
FIG. 6 is a partial section view of a sensor module according to yet another embodiment.

FIG. 6 is a partial section view of a sensor module 400 according to yet another embodiment. A sensor housing 412 includes an inner shell 426 along which diaphragm 422 extends, as generally described above. Housing 412 further includes an outer layer 428, which may be flexible, surrounding and conforming to shell 426 as generally described above. As illustrated in FIG. 6, outer layer 428 of housing 412 may include one or more channels or grooves 440 and 442 having openings along inner surface 430 of layer 428. Grooves 440 are shown extending longitudinally along a length of diaphragm 422, but grooves 440 may extend laterally, diagonally, or curved in alternative embodiments. Grooves 440 are provided to receive medical adhesive applied between diaphragm 422 included in shell 426 and layer 428 to prevent or minimize bulging of outer surface 414. In other embodiments, inner surface 430 of layer 428 may be provided having one or more dimples for receiving medical adhesive, particularly any excess medical adhesive that would otherwise produce bulging of outer surface 414.

Additionally or alternatively, one or more channels 442 may be provided extending between inner surface 430 and outer surface 414 of layer 428 for receiving any excess medical adhesive applied between inner surface 430 and diaphragm 422. A medical adhesive coating applied between inner surface 430 and diaphragm 422 may back fill channel(s) 442 partially or completely to seal housing 420.

Outer layer 428 is also shown to define a shoulder 434 optionally having a sloping upper surface 436 such that outer surface 414 is recessed to alleviate any bulging that may still occur, as described above.

Figure 7:
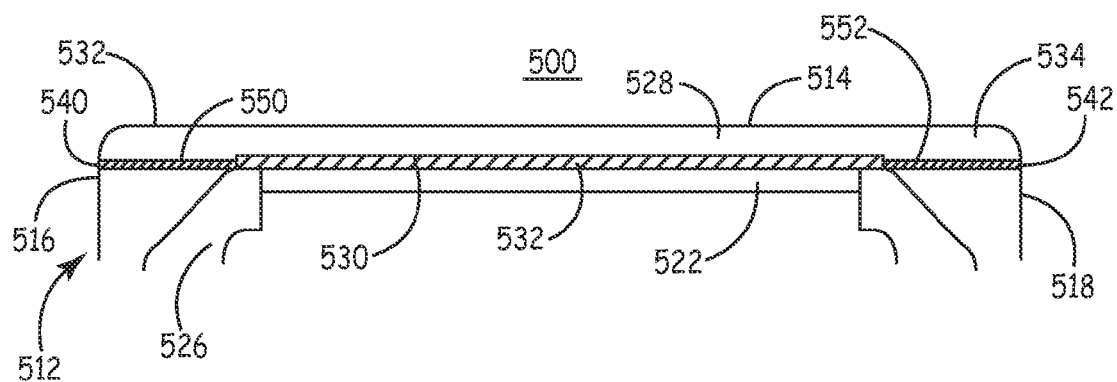
FIG. 7 is a partial sectional view of a sensor module according to still another embodiment.

FIG. 7 is a partial sectional view of a sensor module 500 according to still another embodiment. Housing 512 includes an inner shell 526 having a diaphragm 522 and an outer layer 528. Outer layer 528 includes a recessed inner surface 530 defining a recess 532 between diaphragm 522 and outer layer 528 for receiving medical adhesive applied between diaphragm 522 and layer 528. Outer layer 528 may additionally or alternatively include laterally extending over-fill channels 550 and 552 for receiving any excess medical adhesive applied along recess 532 to prevent or minimize bulging of outer surface 514 over diaphragm 522. In the embodiment shown, over-fill channels 552 extend from recessed inner surface 530 through shoulders 532 and 534 to openings 540 and 542 defined along outer sides 516 and 518, respectively. Over-fill channels 550 and 552 may be partially or fully back-filled during injection of medical adhesive into recess 532 to seal housing 512. It is understood that overfill channels may be included with the flanges shown in the device described above in reference to FIG. 4.

The various features described herein and shown in the accompanying drawings may be used alone or in any combination to reduce contact pressure on a sensor diaphragm. Thus, housings for medical sensor modules have been presented in the foregoing description with reference to specific embodiments. It is appreciated that various modifications to the referenced embodiments may be made without departing from the scope of the disclosure as set forth in the following claims.

The invention claimed is:
1. An implantable medical device, comprising:
a housing having an outer wall and comprising an inner shell and an outer layer formed to extend over and enclose the inner shell to form the outer wall, the inner shell having a thickness extending between an inner wall of the inner shell and an outer wall of the inner shell, the outer layer having an inner side engaged against the outer wall of the inner shell and having a thickness extending between the inner side and the outer wall of the housing, wherein the inner shell and the outer layer form a flat portion;
a flexible diaphragm formed within the inner shell along the flat portion and extending between a first edge and a second edge;
a shoulder extending adjacent to the first edge that extends the outer layer laterally away from a central medial line extending between the first and second edges of the diaphragm;
a recess portion formed between the diaphragm and the inner side of the outer layer; and
an over-fill channel formed by the outer layer and extending through the outer layer from an opening formed at the outer wall to an opening formed along the inner side of the outer layer extending along the flat portion.

2. The device of claim 1, wherein the shoulder is formed by one or both of the inner shell and the outer layer to have a thickness to reduce contact pressure along the first edge and the second edge of the diaphragm to less than a predetermined percentage of a maximum contact pressure along the central median line.

3. The device of claim 2, further comprising a second shoulder extending adjacent to the second edge of the diaphragm that extends the outer layer laterally away from the central medial line extending between the first and second edges of the diaphragm.

4. The device of claim 1, wherein the shoulder comprises a flange extending laterally outward from the outer wall of the housing.

5. The device of claim 4, wherein housing has a rectangular cross-section comprising a top side and a bottom side, the top side corresponding to the flat portion formed by the inner shell and the outer layer.

6. The device of claim 1, wherein the thickness of the outer layer along the shoulder is greater than the thickness of the outer layer along a portion of the outer wall of the housing opposite the flat portion.

7. The device of claim 6, wherein the thickness of the inner shell along the shoulder is approximately equal to the thickness of the inner shell along the portion of the outer wall of the housing opposite the flat portion.

8. The device of claim 1, wherein the thickness of the inner shell along the shoulder is greater than the thickness of the inner shell along a portion of the outer wall of the housing opposite the flat portion.

9. The device of claim 8, wherein the thickness of the outer layer along the shoulder is approximately equal to the thickness of the outer layer along the portion of the outer wall of the housing opposite the flat portion.

10. The device of claim 1, wherein the thickness of the outer layer along the shoulder is greater than the thickness of the outer layer along a portion of the outer wall of the housing opposite the flat portion, and the thickness of the inner shell along the shoulder is greater than the thickness of the inner shell along the portion of the outer wall of the housing opposite the flat portion.

11. The device of claim 10, wherein the thickness of the outer layer along the shoulder is equal to the thickness of the inner shell along the shoulder.

12. The device of claim 1, wherein the over-fill channel extends through the shoulder.

13. An implantable medical device lead, comprising:
an elongated lead body;
a housing having an outer wall and comprising an inner shell and an outer layer formed to extend over and enclose the inner shell to form the outer wall, the inner shell having a thickness extending between an inner wall of the inner shell and an outer wall of the inner shell, the outer layer having an inner side engaged against the outer wall of the inner shell and having a thickness extending between the inner side and the outer wall of the housing, wherein the inner shell and the outer layer form a flat portion;
a flexible diaphragm formed within the inner shell along the flat portion and extending between a first edge and a second edge;
a shoulder extending adjacent to the first edge that extends the outer layer laterally away from a central medial line extending between the first and second edges of the diaphragm;
a recess portion formed between the diaphragm and the inner side of the outer layer; and
an over-fill channel formed by the outer layer and extending through the outer layer from an opening formed at the outer wall to an opening formed along the inner side of the outer layer extending along the flat portion.

14. The implantable medical device lead of claim 13, wherein the shoulder is formed by one or both of the inner shell and the outer layer to have a thickness to reduce contact pressure along the first edge and the second edge of the diaphragm to less than a predetermined percentage of a maximum contact pressure along the central median line.

15. The implantable medical device lead of claim 14, further comprising a second shoulder extending adjacent to the second edge of the diaphragm that extends the outer layer laterally away from the central medial line extending between the first and second edges of the diaphragm.

16. The implantable medical device lead of claim 13, wherein the shoulder comprises a flange extending laterally outward from the outer wall of the housing.

17. The implantable medical device lead of claim 16, wherein housing has a rectangular cross-section comprising a top side and a bottom side, the top side corresponding to the flat portion formed by the inner shell and the outer layer.

18. The implantable medical device lead of claim 13, wherein the thickness of the outer layer along the shoulder is greater than the thickness of the outer layer along a portion of the outer wall of the housing opposite the flat portion.

19. The implantable medical device lead of claim 18, wherein the thickness of the inner shell along the shoulder is approximately equal to the thickness of the inner shell along the portion of the outer wall of the housing opposite the flat portion.

20. The implantable medical device lead of claim 13, wherein the thickness of the inner shell along the shoulder is greater than the thickness of the inner shell along a portion of the outer wall of the housing opposite the flat portion.

21. The implantable medical device lead of claim 20, wherein the thickness of the outer layer along the shoulder is approximately equal to the thickness of the outer layer along the portion of the outer wall of the housing opposite the flat portion.

22. The implantable medical device lead of claim 13, wherein the thickness of the outer layer along the shoulder is greater than the thickness of the outer layer along a portion of the outer wall of the housing opposite the flat portion, and the thickness of the inner shell along the shoulder is greater than the thickness of the inner shell along the portion of the outer wall of the housing opposite the flat portion.

23. The implantable medical device lead of claim 22, wherein the thickness of the outer layer along the shoulder is equal to the thickness of the inner shell along the shoulder.

24. The implantable medical device lead of claim 13, wherein the over-fill channel extends through the shoulder.

* * * * *